United States Patent
Chappaz et al.

(10) Patent No.: US 10,590,060 B2
(45) Date of Patent: Mar. 17, 2020

(54) PROCESS FOR THE PREPARATION OF LEVULINATE ESTERS

(71) Applicants: RHODIA OPERATIONS, Paris (FR); LE CENTRE NATIONAL DE LA RECHERCHE SCIENTIFIQUE, Paris (FR); UNIVERSITE DE POITIERS, Poitiers (FR)

(72) Inventors: Alban Chappaz, Fontaine (FR); Francois Jerome, Sèvres-Anxaumont (FR); Karine De Oliveira Vigier, Fontaine le Comte (FR); Eric Muller, Lyons (FR); Jonathan Lai, Shanghai (CN); Matthieu Corbet, Shanghai (CN); Didier Morvan, Mornant (FR)

(73) Assignees: LE CENTRE NATIONAL DE LA RECHERCHE SCIENTIFIQUE, Paris (FR); UNIVERSITE DE POITIERS, Paris (FR)

( * ) Notice: Subject to any disclaimer, the term of this patent is extended or adjusted under 35 U.S.C. 154(b) by 0 days.

(21) Appl. No.: 16/472,716

(22) PCT Filed: Jun. 30, 2017

(86) PCT No.: PCT/CN2017/091021
§ 371 (c)(1),
(2) Date: Jun. 21, 2019

(87) PCT Pub. No.: WO2018/113240
PCT Pub. Date: Jun. 28, 2018

(65) Prior Publication Data
US 2019/0375703 A1     Dec. 12, 2019

(30) Foreign Application Priority Data

Dec. 21, 2016    (WO) ............... PCT/CN2016/111220
Dec. 21, 2016    (WO) ............... PCT/CN2016/111223

(51) Int. Cl.
C07C 67/29       (2006.01)
C07C 69/716      (2006.01)
B01J 31/22       (2006.01)

(52) U.S. Cl.
CPC ........... *C07C 67/29* (2013.01); *B01J 31/2256* (2013.01); *C07C 69/716* (2013.01); *B01J 2231/49* (2013.01); *B01J 2531/31* (2013.01); *B01J 2531/32* (2013.01); *B01J 2531/42* (2013.01); *B01J 2531/54* (2013.01); *B01J 2531/842* (2013.01)

(58) Field of Classification Search
CPC .... C07C 67/29; C07C 69/716; B01J 31/2256; B01J 2237/49; B01J 2531/31; B01J 2531/32; B01J 2531/42; B01J 2531/54; B01J 2531/842
USPC ....................................................... 560/176
See application file for complete search history.

(56) References Cited

U.S. PATENT DOCUMENTS

| | | | |
|---|---|---|---|
| 7,265,239 B2 | 9/2007 | Van De Graaf | |
| 2005/0171374 A1 | 8/2005 | Manzer | |
| 2007/0049771 A1* | 3/2007 | Van De Graaf | ........ C07C 51/00 562/577 |

FOREIGN PATENT DOCUMENTS

| | | | | |
|---|---|---|---|---|
| CN | 102405205 A | * | 4/2012 | ............. C07C 67/00 |
| CN | 102405205 A | | 4/2012 | |
| CN | 103274942 A | * | 9/2013 | |
| CN | 103274942 A | | 9/2013 | |
| CN | 104959154 A | | 10/2015 | |
| CN | 105646227 A | | 6/2016 | |
| CN | 105728042 A | | 7/2016 | |
| CN | 105884616 A | | 8/2016 | |
| WO | 2007023173 A1 | | 3/2007 | |

OTHER PUBLICATIONS

Search Report for International Application No. PCT/CN2017/091021 dated Sep. 28, 2017.
Search Report for International Application No. PCT/CN2016/111220 dated Apr. 25, 2017.
Search Report for International Application No. PCT/CN2016/111223 dated May 4, 2017.

* cited by examiner

*Primary Examiner* — Deborah D Carr
(74) *Attorney, Agent, or Firm* — Pearne & Gordon LLP

(57) ABSTRACT

A process for synthesizing at least one levulinate ester, said process comprising the reaction of furfuryl alcohol with at least one other alcohol in the presence of water and at least one catalyst, said furfuryl alcohol being present in a quantity of at least 5% by weight, based on the total weight of the alcohols, and said catalyst comprising at least one triflate ligand and at least one metal selected from bismuth, gallium, aluminum, tin and iron.

15 Claims, No Drawings

PROCESS FOR THE PREPARATION OF LEVULINATE ESTERS

CROSS-REFERENCE TO RELATED APPLICATIONS

This is a National Stage application of PCT international application PCT/CN2017/091021, filed on Jun. 30, 2017, which claims the priority of China PCT Patent Application No. PCT/CN2016/111220, filed Dec. 21, 2016 and China PCT Patent Application No. PCT/CN2016/111223, filed Dec. 21, 2016, all of which are incorporated herein by reference in their entirety.

TECHNICAL FIELD

The present invention relates to a process for the preparation of levulinate esters starting from furfuryl alcohol or from furfural in the presence of specific Lewis acid catalysts.

BACKGROUND ART

Levulinate esters, such as alkyl levulinates, are industrially relevant solvents or intermediates for the manufacture of pesticides, plasticizers, polymers or fuel additives. The acid-catalyzed ring opening of furfuryl alcohol in alcoholic media is a reaction of high interest yielding alkyl levulinates.

In contrast to the classical route involving 5-hydroxymethylfurfural (HMF) as a starting reagent or intermediate, alkyl levulinates can be produced from furfuryl alcohol through an elegant 100% atom economical process. Furthermore, furfuryl alcohol is industrially produced in large scale from the manufacture of hemicellulosic biomass. The selectivity of the catalytic production of alkyl levulinates from furfuryl alcohol is rather low due to the dominant acid-catalyzed side polymerization of furfuryl alcohol leading to an important formation of tar.

Document WO 2010/102203 discloses a method for the preparation of alkyl levulinates starting from furfuryl alcohol and an alkanol in the presence of a protic acid such as hydrochloric acid or sulfuric acid. A mixture alkyl levulinate/alkanol instead pure alkanol is used as a solvent for dilution of the furfuryl alcohol. The catalysts used in this document are generally not easily recyclable since tarry products are formed when the concentration of furfuryl alcohol is increased.

J. R. Kean and A. E. Graham, Catalysis Communications 59 (2015) 175-179, discloses a method for synthesizing alkyl levulinates from furfuryl alcohols using Indium(III) triflate catalysts. The amount of furfuryl alcohol introduced in the process of said document is relatively low.

To inhibit side polymerization reactions, previously reported homogeneous or heterogeneous catalytic processes are conducted under diluted conditions (furfuryl alcohol loading of 2-3 wt %).

Yao-Bing Huang et al. (Green Chem. 2016, 18, 1516-1523) discloses the conversion of furfuryl alcohol into alkyl levulinates catalyzed by metal salts comprising halogen or sulfated oxides, such as $SnCl_4$ or $AlCl_3$ catalysts. It has been observed that catalysts of type $SnCl_4$ or $AlCl_3$ provide the conversion with a relatively low productivity.

It was thus an object of the present invention to develop a process for converting furfuryl alcohol into levulinate esters with a catalytic system that permits to get very high selectivities and productivities.

SUMMARY OF THE INVENTION

A first object of the invention is a process for synthesizing at least one levulinate ester, said process comprising the reaction of furfuryl alcohol with at least one other alcohol in the presence of water and at least one catalyst, said furfuryl alcohol being present in a quantity of a least 5% by weight, based on the total weight of the alcohols, said catalyst comprising at least one triflate ligand and at least one metal selected from bismuth, gallium, aluminum, tin and iron.

According to an embodiment of the invention, the catalyst further comprises at least one (other) ligand selected from triflate, triflimidate, halogen, alkoxy, sulfate, nitrate, carboxylate, alkyl, aryl, metal, hydroxide, hydride or acetylacetonate ligands, preferably from triflate, triflimidate, halogen, more preferably from triflate.

Preferably, the catalyst is selected from $SnX^1X^2X^3(OTf)$ and $MX^1X^2(OTf).xH_2O$ wherein:
M represents a metal selected from Bi, Ga and Al,
$X^1$, $X^2$, and $X^3$ represent independently to each other a ligand, preferably selected from triflate, halogen, alkoxy, sulfate, nitrate, carboxylate, $-N(SO_2CF_3)_2$, alkyl, aryl, metal ligands, more preferably from triflate and halogen ligands;
OTf represents a triflate; and
x ranges from 0 to 10, preferably x is zero.

According to an embodiment, the catalyst is selected from $Sn(OTf)_4$, $Bi(OTf)_3$ and $BiCl_2OTf$, preferably from $Bi(OTf)_3$ and $BiCl_2OTf$, more preferably from $Bi(OTf)_3$.

According to an embodiment of the invention, the catalyst is in an anhydrous form.

According to an embodiment of the invention, the furfuryl alcohol is present in a quantity ranging from 5 to 50% by weight, preferably from 7 to 40% by weight, more preferably from 10 to 25% by weight, based on the total weight of the alcohols.

According to an embodiment, the furfuryl alcohol is obtained from the reduction of furfural. Preferably, the process is performed in two steps, the first step being the reduction of furfural into furfuryl alcohol and the second step comprising the addition of the other alcohol for the reaction between furfuryl alcohol and the other alcohol.

According to an embodiment of the invention, the catalyst is present in an amount ranging from 0.05 to 20% mol, preferably ranging from 0.1 to 10% mol, more preferably ranging from 0.5 to 5% mol relative to the molar amount of furfuryl alcohol.

According to an embodiment of the invention, the molar ratio water/(metal of the catalyst) ranges from 0.1 to 20, preferably from 0.3 to 10, more preferably from 0.5 to 5.

According to an embodiment of the invention, the other alcohol is selected from alcohols of formula ROH wherein R is selected from linear, branched, cyclic, saturated or unsaturated hydrocarbyl radicals. Preferably, R comprises from 1 to 30 carbon atoms, preferably from 2 to 24 carbon atoms, more preferably from 3 to 16 carbon atoms.

According to an embodiment of the invention, the other alcohol is in the form of a solution comprising only one alcohol or at least two different alcohols.

According to an embodiment of the invention, the process comprises the following steps:
a) providing a reaction mixture comprising all or part of the catalyst, all or part of the water, and all or part of the other alcohol,
b) introducing all or part of the furfuryl alcohol and optionally the remaining part of the other alcohol into the reaction mixture in order to synthesize the levulinate esters,
c) recovering the levulinate esters.

Preferably, the process further comprises a step of heating the reaction mixture obtained at the end of step a) to a temperature ranging from 80° C. to 200° C., preferably from 100° C. to 180° C., more preferably from 115° C. to 165° C.

The process of the present invention permits to works with highly concentrated furfuryl alcohol solutions, as high as 5% or 10% by weight or even as high as 50% by weight of furfuryl alcohol in the reaction medium.

The process of the present invention allows obtaining a high yield, such as 94% yield of levulinate esters, as well as a high productivity.

The process of the present invention allows reducing the amount of by-products that can be formed during the reaction.

The produced levulinate esters are stable and can be conveniently recovered from the reaction medium, for example by distillation, and the catalyst can be recycled for a further conversion reaction.

DETAILED DESCRIPTION OF THE INVENTION

The present invention is directed to a process for synthesizing at least one levulinate ester, said process comprising the reaction of furfuryl alcohol with at least one other alcohol in the presence of water and at least one catalyst, said furfuryl alcohol being present in a quantity of a least 5% by weight, based on the weight of all alcohol, and said catalyst comprising at least one triflate ligand and at least one metal selected from bismuth, gallium, aluminum, tin and iron.

Preferably, the catalyst comprises at least one metal selected from bismuth, gallium, aluminum and tin, more preferably from bismuth and tin, even more preferably from bismuth.

The catalyst used in the present invention comprises at least one first triflate ligand. Within the meaning of the present invention, the triflate, also named trifluoromethanesulfonate, represents $CF_3SO_3-$.

According to an embodiment of the invention, the catalyst further comprises at least one second ligand selected from triflate (OTf), triflimidate ($NTf_2$), halogen, alkoxy, sulfate, nitrate, carboxylate, alkyl, aryl, metal, hydroxide, hydride or acetylacetonate ligands, preferably the catalyst comprises at least one second ligand selected from triflate (OTf), triflimidate ($NTf_2$), halogen, more preferably from triflate.

Among metal ligands, mention may be made of Re, Pd, Fe, Ga, Sm, Co, Bi. Indeed, the catalyst can be in a dimeric form, including for example a Bi—Bi or Bi—Pd bound.

Among halogen ligands, mention may be made of chloride, bromide, fluoride or iodide ligands, and preferably chloride ligands.

Among alkoxy ligands, mention may be made of alkoxy ligands of formula —OR' wherein R' represents an alkyl radical comprising from 1 to 24 carbon atoms or an alkenyl radical comprising from 2 to 24 carbon atoms, said alkyl and alkenyl radicals can be linear, branched or cyclic and can optionally comprise one or more heteroatoms, such as oxygen, sulfur or nitrogen, for example in a side chain. According to a specific embodiment, the alkoxy ligand is selected from methoxy, ethoxy, propoxy, butoxy ligands.

As is well known for the skilled person, "Tf" represents a triflyl group also named trifluoromethanesulfonyl ($CF_3SO_3-$). Therefore, $NTf_2$ represents the triflimidate radical —$N(SO_2CF_3)_2$.

Among alkyl ligands, mention may be made of alkyl or alkenyl radicals having from 1 to 24 carbon atoms, said alkyl and alkenyl radicals can be linear, branched or cyclic. Alkyl ligands may optionally comprise one or more heteroatoms, such as oxygen, sulfur or nitrogen, for example in a side chain. According to a specific embodiment, the alkyl ligand is selected from methyl, ethyl, propyl, butyl, pentyl, cyclopentadienyl ligands.

Among aryl ligands, mention may be made of aryl radicals having from 6 to 24 carbon atoms, said aryl radical can be substituted by one or more substituents, such as alkyl or alkenyl having from 1 to 12 carbon atoms, said aryl radical can be bicyclic. According to a specific embodiment, the aryl radical is selected from phenyl, benzyl, naphthenyl.

Among carboxylate ligands, mention may be made of carboxylate of formula —OCOR'' wherein R'' represents an alkyl radical comprising from 1 to 24 carbon atoms or an alkenyl radical comprising from 2 to 24 carbon atoms, said alkyl and alkenyl radicals can be linear, branched or cyclic and can optionally comprise one or more heteroatoms, such as oxygen, sulfur or nitrogen, for example in a side chain. According to a specific embodiment, carboxylate ligands are selected from methanoate, acetate, propanoate, butanoate ligands.

According to an embodiment of the invention, the catalyst may further comprise at least one organic ligand of type "L", i.e. a neutral ligand that donate two electrons to the metal, the bond between these ligands and the metal is a coordinate bond. As an example of organic ligand of type L, mention may be made of phosphine ligands, in particular diphosphine ligands, such as 1,2-bis(diphenylphosphino)ethane (DPPE) or diamine ligands, in particular bipyridine. The presence of this kind of organic ligand may improve the selectivity towards levulinate esters and may allow introducing a higher amount of furfuryl alcohol in the reaction medium. Ligands may also improve the solubility of the catalyst, the stability of the catalyst or the kinetics of the reaction.

According to an embodiment, the catalyst is selected from $Bi(OTf)_3$, $Ga(OTf)_3$, $Al(OTf)_3$, $Sn(OTf)_4$, and $BiCl_2(OTf)$, more preferably from $Bi(OTf)_3$, $Sn(OTf)_4$ and $BiCl_2(OTf)$, even more preferably from $Bi(OTf)_3$.

Catalysts that can be used in the process of the invention are commercially available or may be synthesized by processes well known for the skilled person.

The catalyst used in the process of the invention may be unsupported (homogeneous catalysis) or supported (heterogeneous catalysis). A supported catalyst facilitates the process and the recovery of the catalyst at the end of the reaction and does not change the catalysis cycle or the role of the catalyst during the reaction. The support may be any support well known by the skilled person in the art, such as silica, alumina, zeolites or titanium-based solids, or metal oxides such as bismuth oxides, gallium oxides, tin oxides, aluminum oxides or iron oxides. Among supports, mention may also be made of polystyrene resins, acid oxides, such as niobium oxides, zeolites or sulfonated charcoals.

The catalyst may also be immobilized in a liquid phase.

According to an embodiment, one or more other catalysts, different from the (Lewis acid) catalysts defined above may be also present in the reaction medium. Preferably, said other catalysts are selected from Bronsted acids, in particular strong Bronsted acids, such as triflic acid, perfluorosulfonic acid (Aquivion®) or Nafion®. Nafion is well known by the skilled person and can be defined as a sulfonated tetrafluoroethylene based fluoropolymer-copolymer.

The combination of said Bronsted acid with the Lewis acid catalyst defined above and used in the process of the invention provides a synergistic effect for improving the selectivity towards the levulinate esters.

According to an embodiment, the catalyst(s) is(are) present in an amount ranging from 0.05 to 5% mol, preferably ranging from 0.1 to 3% mol, more preferably ranging from 0.5 to 2% mol based on the molar amount of furfuryl alcohol.

The reaction takes place in the presence of a catalytic amount of water. According to an embodiment, the reaction takes place with a molar ratio water/metal M (metal of the catalyst) ranging from 0.1 to 20, preferably from 0.3 to 10, more preferably from 0.5 to 5.

Water may for example be introduced into the reaction medium by an addition of (external) water or through the use of a catalyst in the form of a hydrate. Nevertheless, the catalyst will be preferably in an anhydrous form, in this embodiment, in the formula $MX^1X^2(OTf).xH_2O$ defined above, x is equal to zero.

By "reaction medium", it is to be understood the medium wherein the reaction takes place. The reaction medium comprises the furfuryl alcohol, at least one other alcohol (different from furfuryl alcohol), the catalyst(s) and water. The reaction medium may further optionally comprise additional additives such as solvents different from the reactants of the conversion reaction.

According to an embodiment, the reaction medium is substantially free, or even totally free, of organic solvents different from the reactants (in particular different from the other alcohol reacting with the furfuryl alcohol) and the catalyst of the conversion reaction.

The conversion reaction of furfuryl alcohol to levulinate ester may be represented by the following equation:

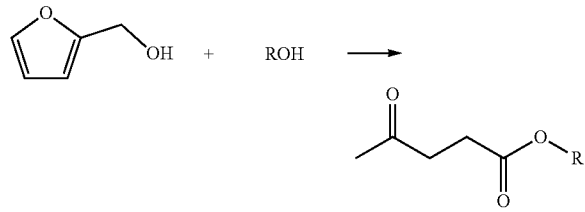

wherein ROH represents the other alcohol which reacts with the furfuryl alcohol.

According to an embodiment, furfuryl alcohol is obtained from the reduction of furfural. The reduction of furfural may be represented by the following equation:

The reduction of furfural into furfuryl alcohol may be performed in the presence of hydrogen (or by hydrogen transfer) and a catalyst suitable for performing said reaction. Such catalysts are well known for the skilled person, among those catalysts for the reduction of furfural, mention may be made as an example of copper based catalysts. The reduction may be performed in the presence of a solvent, said solvent may be for example the other alcohol which will be used in the reaction of conversion of furfuryl alcohol into levulinate ester.

Furfuryl alcohol and furfural may be commercially available. Furfuryl alcohol may be of natural or synthetic origin.

According to an embodiment, the furfuryl alcohol may be purified before introduction into the reaction medium, by purification methods well known for the skilled person.

The furfuryl alcohol is present in a quantity of at least 5% by weight, preferably in an amount ranging from 5 to 50% by weight, more preferably from 7 to 40% by weight, even more preferably from 10 to 25% by weight, based on the total weight of all the alcohols present in the reaction medium.

The expression "all the alcohols" refers to the furfuryl alcohol and the other alcohol(s) used in the reaction medium for the conversion of furfuryl alcohol into levulinate ester(s).

The other alcohol which reacts with furfuryl alcohol may be selected from aliphatic alcohols or aromatic alcohols, preferably from aliphatic alcohols.

An aliphatic alcohol is a non-aromatic alcohol. An aromatic alcohol comprises a OH function directly linked to an aryl ring. An example of an aromatic alcohol is a phenol.

The other alcohol may be a monol or a polyol comprising for example from 2 to 5 OH functions or from 2 to 4 OH functions or from 2 to 3 OH functions, preferably the other alcohol is a monol, i.e. an alcohol comprising only one OH function.

According to an embodiment, the other alcohol is introduced through an alcoholic solution that may comprise one or several different alcohols, preferably the alcoholic solution comprises only one alcohol. In the case wherein the alcoholic solution comprises a mixture of different alcohols, the levulinate esters obtained at the end of the reaction may be a mixture of different levulinate esters.

According to an embodiment, the other alcohol is selected from primary alcohols, i.e. compounds comprising at least the following radical: —$CH_2$—OH.

According to an embodiment, the other alcohol is of formula ROH wherein R is selected from linear, branched, cyclic, saturated or unsaturated hydrocarbyl radicals.

By "hydrocarbyl radical", it is to be understood a radical comprising carbon atoms and hydrogen atoms, and optionally heteroatoms such as oxygen, nitrogen or sulfur.

According to an embodiment, the hydrocarbyl radicals consist in carbon atoms and hydrogen atoms.

According to an embodiment, the other alcohol comprises from 1 to 30 carbon atoms, preferably from 2 to 24 carbon atoms, more preferably from 3 to 16 carbon atoms.

According to an embodiment, the other alcohol is selected from methanol, ethanol, propanol, isopropanol, butanol, pentanol, hexanol, heptanol, octanol, decanol, dodecanol.

The other alcohol may be introduced in a stoichiometric amount in relation to the furfuryl alcohol or in excess, in particular if the other alcohol is also used as a solvent for example for preparing the catalyst in the reaction medium.

According to an embodiment, the reaction is performed at a temperature ranging from 80° C. to 200° C., preferably from 100° C. to 180° C., more preferably from 115° C. to 165° C.

The reaction is generally performed at a pressure such that the reactants remain in a liquid state. Preferably, the reaction is performed at a pressure ranging from 0.5 to 5 bars, preferably from 1 to 3 bars, more preferably at atmospheric pressure.

According to an embodiment, the process of the invention comprises the following successive steps:

a) providing a reaction mixture comprising all or part of the catalyst, all or part of the water, and all or part of the other alcohol, b) introducing all or part of the furfuryl alcohol and optionally the remaining part of the other alcohol into the reaction mixture in order to synthesize the levulinate esters, c) recovering the levulinate esters.

According to an embodiment of the invention, the reaction mixture obtained in step a) comprises all of the catalyst used in the reaction and/or all the water used in the reaction.

According to an embodiment of the invention, the reaction mixture, before step b), is heating to a temperature ranging from 80° C. to 200° C., preferably from 100° C. to 180° C., more preferably from 115° C. to 165° C. This heating step may help for the preparation of the catalyst.

According to an embodiment of the invention, water is added into the reaction mixture before step b) and before the heating of said reaction mixture if any.

According to an embodiment of the invention, all the furfuryl alcohol is introduced during step b).

According to an embodiment, furfuryl alcohol is mixed with the remaining part of the other alcohol before its introduction into the reaction mixture obtained in step a).

The process of the reaction may be a batch process or a continuous process. Indeed, furfuryl alcohol may be sequentially or continuously introduced into the reaction mixture obtained at step a). The sequentially or continuously addition allows improving the selectivity towards levulinate esters and allows loading a higher amount of furfuryl alcohol into the reaction medium.

At the end of the reaction, levulinate esters and other products can be recovered and isolated, for example by distillation.

The catalyst may be recycled for performing another reaction and another process.

The reaction can be followed by gas chromatography or by HPLC (high performance liquid chromatography) or also by $^1$H or $^{13}$C NMR (Nuclear magnetic resonance), according to well-known methods for the skilled person.

The process of the invention generally leads to a yield in levulinate ester of at least 40% mol, preferably at least 45% mol, more preferably at least 50% mol, even more preferably at least 55% mol, based on moles of furfuryl alcohol in the reaction medium.

The following examples show the effectiveness of the process and further explain the process of the present invention.

Should the disclosure of any patents, patent applications, and publications which are incorporated herein by reference conflict with the description of the present application to the extent that it may render a term unclear, the present description shall take precedence.

EXAMPLES

General Description of the Process of the Present Examples

In a typical experiment, a 100 mL glass reactor containing water (0.10 mmol, 1 eq. as compared to the metal of the catalyst), the catalyst (0.10 mmol, 1 mol %) and 5.78 g of butanol were stirred and heated to reflux (118° C.). Then a solution containing 1.0 g of furfuryl alcohol (10.2 mmol) and 3.0 g of butanol (40.4 mmol) was introduced in the reactor.

Samples (0.1 g) were taken from the reaction mixture after different times and quenched with 1.1 g of isopropanol. An aliquot of the sample was filtered on Nylon Acrodisc 0.2 μm and analysed by GC without any further treatments.

The catalyst has been added in a proportion such that for each experiment, the catalyst represents 1% mol.

Example 1: Comparison of Different Catalysts

Furfuryl alcohol is present in an amount of 10% wt and the catalyst is present in an amount of 1% mol with regard to furfuryl alcohol.

For each experiment, 1 molar equivalent of water, as compared to the furfuryl alcohol, has been added before heating.

The yield (or selectivity) in butyl levulinate corresponds to the amount of butyl levulinate expressed in molar percentage based on the molar amount of furfuryl alcohol introduced into the reaction medium.

The productivity is the mol of butyl levulinate per mol of catalyst and per hour.

In the tables below, the following abbreviations have been used:

TABLE 1

Characteristics of the process for different catalysts

| Catalyst | amount of catalyst (mg) | Time (h) | BL Yield (%) | Productivity (mol(BL)/h/mol(cata)) |
|---|---|---|---|---|
| Nafiong | 100 | 3.8 | 35 | |
| In(OTf)$_3$ | 56 | 1.2 | 33 | 24.5 |
| Sc(OTf)$_3$ | 49 | 2.8 | 39 | 14.6 |
| AlCl$_3$.6H$_2$O | 24 | 3 | 45 | 14.9 |
| Ga(OTf)$_3$ | 52 | 2 | 59 | 27.3 |
| SnCl$_4$.5H$_2$O | 28 | 3.5 | 60 | 17.7 |
| Sn(OTf)$_4$ | 71 | 1 | 60 | 24.1 |
| Bi(OTf)$_3$ | 66 | 0.7 | 60 | 92.2 |

As illustrated in table 1, the Lewis acid catalysts based on Bi and Ga allow the production of butyl levulinates with a yield improved as compared to the acid catalysts based on In or Sc. Previous works were limited to a furfuryl alcohol content of only 2 wt % solutions to achieve similar results. The possibility to use a solution containing a higher amount of furfuryl alcohol is industrially more interesting in terms of operating costs.

Additionally, the catalysts Bi(OTf)$_3$, Sn(OTf)$_4$ and Ga(OTf)$_3$ comprising a triflate ligand allow the production of butyl levulinates with a productivity improved as compared to catalysts comprising chlorine ligands.

Example 2: Process with Different Amounts of Furfuryl Alcohol

The same procedure has been conducted with Bi(OTf)$_3$ as catalyst but with different amounts of furfuryl alcohol following two protocols, one in batch wherein all the FAA is added at the beginning, and the second wherein the FAA is added dropwise over 2 h. The characteristics of the process are indicated in table 2 below.

For each experiment, 1 equivalent of water, as compared to the catalyst, has been added.

TABLE 2

Characteristic of the process for different amounts of furfuryl alcohol

| Total FFA loading (% wt) | FAA addition protocol | reaction time including addition Time (h) | BL yield (%) | Productivity (mol.h$^{-1}$.mol cata$^{-1}$) |
|---|---|---|---|---|
| 10 | Batch | 0.7 | 60 | 92.2 |
| 5 | Dropwise | 2.5 | 97 | 18.3 |
| 7.5 | Dropwise | 2.5 | 96 | 36.2 |
| 10 | Dropwise | 2.5 | 94 | 37.3 |
| 20 | Dropwise | 2.5 | 95 | 38.1 |
| 30 | Dropwise | 2.5 | 92 | 49.5 |

As illustrated in table 2, the reaction can be performed with a relatively high amount of furfuryl alcohol. Indeed, with an amount of 30% by weight of furfuryl alcohol, the yield is still of 92%.

Example 3: Process with Different Alcohols

The same procedure as in example 1, using Bi(OTf)$_3$ as catalyst, was applied replacing n-butanol respectively by methanol, ethanol and isopropanol as starting alcohol. Corresponding alkyls levulinates yields were measured after 0.7 h reaction.

Irrespective of the starting alcohol, corresponding alkyl levulinates were all obtained in 60% yields.

Example 4: Variation of the Amount of Water

In a 100 mL glass reactor, 66 mg of Bi(OTf)$_3$ (0.10 mmol, 1 mol %), an appropriate amount of water (reported in table 3) and 5.77 g of n-butanol were stirred and heated under reflux (117° C.). Then a solution containing 1.0 g of furfuryl alcohol (10.2 mmol) and 4.0 g of n-butanol was introduced in the reactor.

The amount of water added (external water) is expressed in equivalent (eq.) of water as compared to Bi(OTf)$_3$ (first column of table 3).

TABLE 3

Characteristic of the process for different amounts of water

| Added H$_2$O (eq.) | Reaction time (h) | Conv. FFA (%) | BL Yield (%) |
|---|---|---|---|
| 0 | 0.7 | 100 | 50 |
| 0.5 | 1.0 | 100 | 67 |
| 1 | 0.7 | 100 | 80 |
| 5 | 0.7 | 100 | 75 |
| 50 | 0.7 | 100 | 59 |
| 250 | 2.5 | 100 | 61 |
| 1000 | 4.5 | 100 | 60 |

It is clear from the results reported in Table 3 that the presence of water improved the yield of butyl levulinate. Moreover, the results show that the molar ratio water/metal M (metal of the catalyst) had strong influence onto the yield.

Example 5: Recycling of Bi(OTf)$_3$ Catalyst

The same reaction procedure as example 1, using Bi(OTf)$_3$ as catalyst, was applied. Yields are reported after 0.7 h reaction in table 4. After each run, excess of n-butanol and BL were recovered by fractional distillation. Then fresh FFA and the distilled n-butanol were added to the distillation residue comprising some unidentified black solids and the recycled Bi(OTf)$_3$ catalyst. After the third cycle, it was necessary to remove the black solids by filtration to facilitate the long term recycling of the catalytic residue.

TABLE 4

Results of the recycling Bi(OTf)$_3$ as catalyst

| Run | 1 | 2 | 3 | 4 | 5 | 6 |
|---|---|---|---|---|---|---|
| Butyl levulinate Yield (%) | 60 | 57 | 58 | 58 | 60 | 54 |
| FFA Conversion (%) | 100 | 100 | 100 | 100 | 100 | 100 |

The Bi(OTf)$_3$ catalyst was found to be successfully recycled at least 6 times without apparent decrease of the reaction yield and activity.

Example 6: Effect of the Ligand

The (DPPE)BiCl$_2$(OTf) catalyst was synthesized following the work of S. S. Chitnis, N. Burford, A. Decken, M. J. Ferguson, *Inorg. Chem.* 2013, 52, 7242-7248, by replacing the 1,2 Bis(dimethylphosphino)ethane (DMPE) by 1,2-Bis (diphenylphosphino)ethane (DPPE).

In a typical experiment, a 100 mL glass reactor containing 88 mg of (DPPE)BiCl$_2$(OTf) (0.10 mmol, 1 mol %), 0.18 g of water (10 mmol, 2 wt %=100 eq./Bi metal) and 4.4 g of butanol were stirred and heated under reflux (117° C.). Then the right amount of furfuryl alcohol to reach the concentration in reported in table 5 was introduced in the reactor.

TABLE 5

Catalytic conversion of FFA to BL in the presence of (DPPE)BiCl$_2$(OTf).

| Entry | FFA concentration (wt %) | Time (h) | Catalyst amount (mol %) | BL Yield (%) |
|---|---|---|---|---|
| 1 | 10 | 21.5 | 1.0 | 92 |
| 2 | 20 | 22.5 | 0.5 | 94 |
| 3 | 30 | 26.0 | 0.3 | 71 |

The results compiled in table 5 shows that different ligands could be used successfully. It is worthy to note that the catalyst amount is kept the same in each entry explaining why the catalyst ratio decreases along with an increase of FFA concentration.

What is claimed is:

1. A process for synthesizing at least one levulinate ester, said process comprising the reaction of furfuryl alcohol with at least one other alcohol in the presence of water and at least one catalyst, said furfuryl alcohol being present in a quantity of a least 5% by weight, based on the total weight of the alcohols, and said catalyst comprising at least one triflate ligand and at least one metal selected from bismuth, gallium, aluminum, tin and iron.

2. The process according to claim 1, wherein the metal of the catalyst is selected from bismuth and gallium.

3. The process according to claim 1, wherein the catalyst is selected from SnX1X2X3(OTf) and MX1X2(OTf).xH20 wherein:
   M represents a metal selected from Bi, Ga and Al,
   X1, X2, and X3 represent independently to each other a ligand, selected from triflate, halogen, alkoxy, sulfate, nitrate, carboxylate, —N(SO2CF3)2, alkyl, aryl, metal ligands;

OTf represents a triflate; and x ranges from 0 to 10.

4. The process according to claim 1, wherein the catalyst is selected from Bi(OTf)3 and BiCl2OTf.

5. The process according to claim 1, to wherein the catalyst is in an anhydrous form.

6. The process according to claim 1, wherein furfuryl alcohol is present in a quantity ranging from 5 to 50% by weight, based on the total weight of the alcohols.

7. The process according to claim 1, wherein the furfuryl alcohol is obtained from the reduction of furfural.

8. The process according to claim 7, wherein said process is performed in two steps, the first step being the reduction of furfural into furfuryl alcohol and the second step comprising the addition of the other alcohol for the reaction between furfuryl alcohol and the other alcohol.

9. The process according to claim 1, wherein the catalyst is present in an amount ranging from 0.05 to 20% mol, relative to the molar amount of furfuryl alcohol.

10. The process according to claim 1, wherein the molar ratio water/metal of the catalyst ranges from 0.1 to 20.

11. The process according to claim 1, wherein the other alcohol is selected from alcohols of formula ROH wherein R is selected from linear, branched, cyclic, saturated or unsaturated hydrocarbyl radicals.

12. The process according to claim 11, wherein R comprises from 1 to 30 carbon atoms.

13. The process according to claim 1, wherein the other alcohol is in the form of a solution comprising only one alcohol or at least two different alcohols.

14. The process according to claim 1, comprising the following steps:
    a) providing a reaction mixture comprising all or part of the catalyst, all or part of the water, and all or part of the other alcohol,
    b) introducing all or part of the furfuryl alcohol and optionally the remaining part of the other alcohol into the reaction mixture in order to synthesize the levulinate esters,
    c) recovering the levulinate esters.

15. The process according to claim 14, further comprising a step of heating the reaction mixture obtained at the end of step a) to a temperature ranging from 80° C.

* * * * *